United States Patent [19]

Wesseling et al.

[11] Patent Number: 4,539,997

[45] Date of Patent: Sep. 10, 1985

[54] METHOD AND DEVICE FOR CONTROLLING THE CUFF PRESSURE IN MEASURING THE BLOOD PRESSURE IN A FINGER BY MEANS OF PHOTO-ELECTRIC PLETHYSMOGRAPH

[75] Inventors: Karel H. Wesseling, Bunnik; Benjamino de Wit, Kerk Avezaath, both of Netherlands

[73] Assignee: Nederlandse Centrale Organisatie voor Toegepast-Natuurwetenschappelijk Onderzoek, The Hague, Netherlands

[21] Appl. No.: 437,026

[22] Filed: Oct. 27, 1982

[30] Foreign Application Priority Data

Oct. 28, 1981 [NL] Netherlands ............. 8104879

[51] Int. Cl.³ ................................. A61B 5/02
[52] U.S. Cl. ..................... 128/667; 128/677; 128/681
[58] Field of Search ............. 128/665–667, 128/680–681, 672, 677, 687, 691

[56] References Cited

U.S. PATENT DOCUMENTS 4,105,021  8/1978  Williams et al. ............. 128/683

FOREIGN PATENT DOCUMENTS 2070240  9/1981  United Kingdom ............. 128/666

OTHER PUBLICATIONS

IEEE Transactions on Biomedical Engineering, vol. BME-27, No. 3, Mar. 1980 (Yamakoshi, Shimazu, Togawa), pp. 150–155.

Primary Examiner—Lee S. Cohen
Assistant Examiner—Angela D. Sykes
Attorney, Agent, or Firm—Cushman, Darby & Cushman

[57] ABSTRACT

Arrangement for controlling the cuff pressure in the indirect, non-invasive, continuous measurement of blood pressure in a finger by using a photo-electric plethysmograph in a fluid-filled pressure cuff, an electronic control circuit and an electric pressure valve, the cuff pressure being controlled by the plethysmographic signal in closed-loop operation by means of a servo-reference level, so that the arterial volume is maintained at a pre-adjusted value. For initial adjustment, the cuff pressure or the servo-reference level as initial adjustment quantity is automatically changed continuously in the control range by means of a control waveform supplied to the electronic control circuit, that thereby the peak-through amplitude of the pulsatile plethysmographic signal or cuff pressure signal is detected time and again, and compared with the preceding peak-through amplitude. The biggest value thereof in the control range and the associated value of the cuff pressure at servo-reference level are stored, which value of cuff pressure or servo-reference at the end of the initial adjustment is used as set value for the measurement of the blood pressure.

15 Claims, 3 Drawing Figures

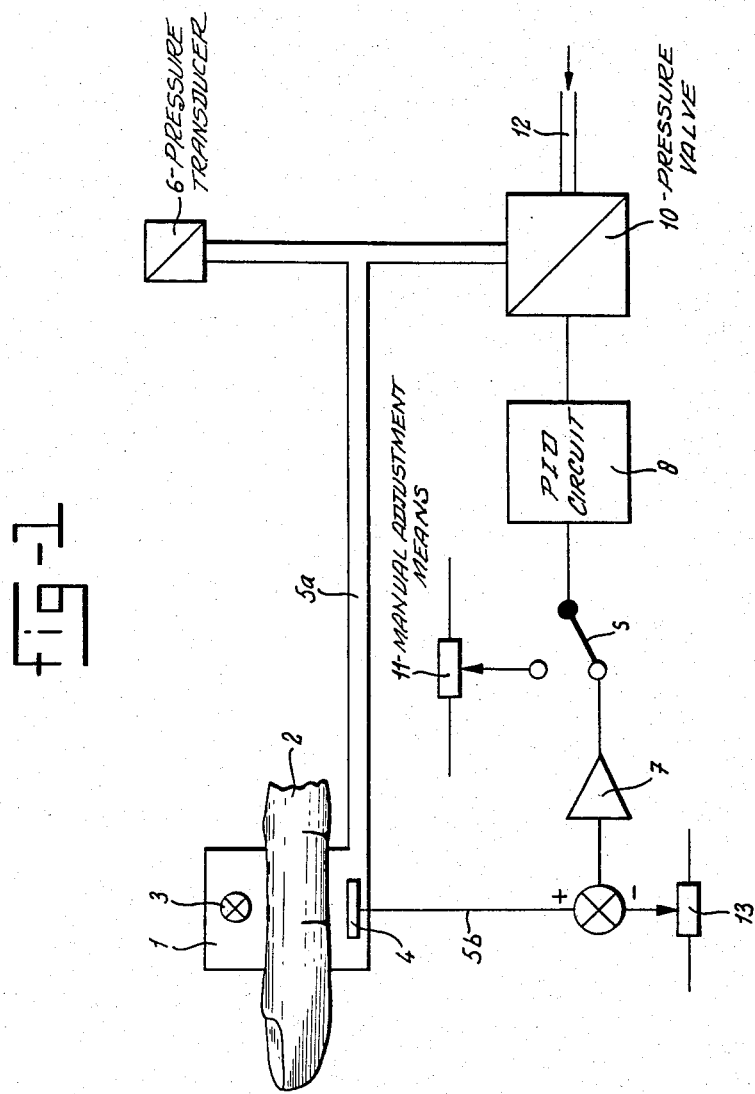

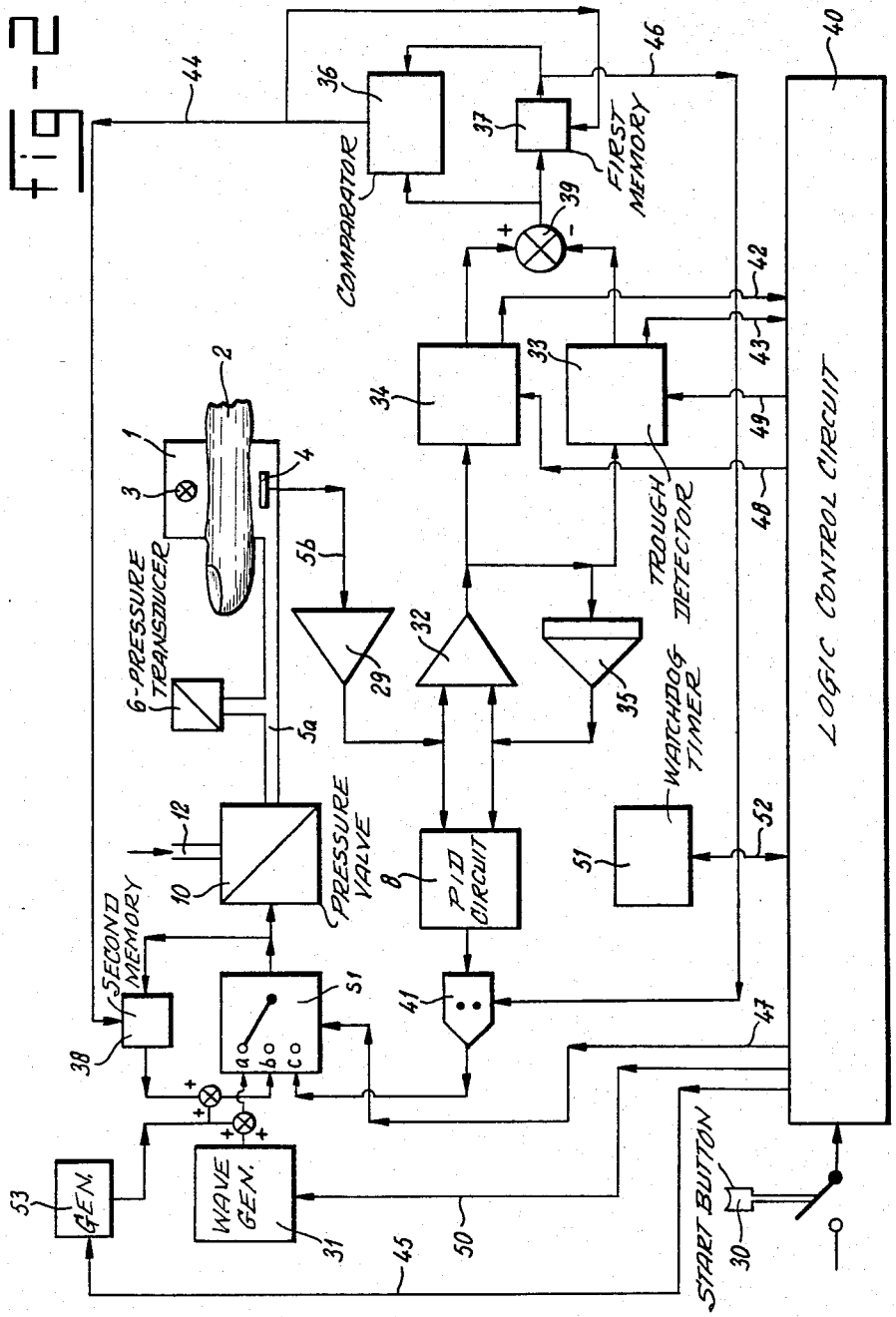

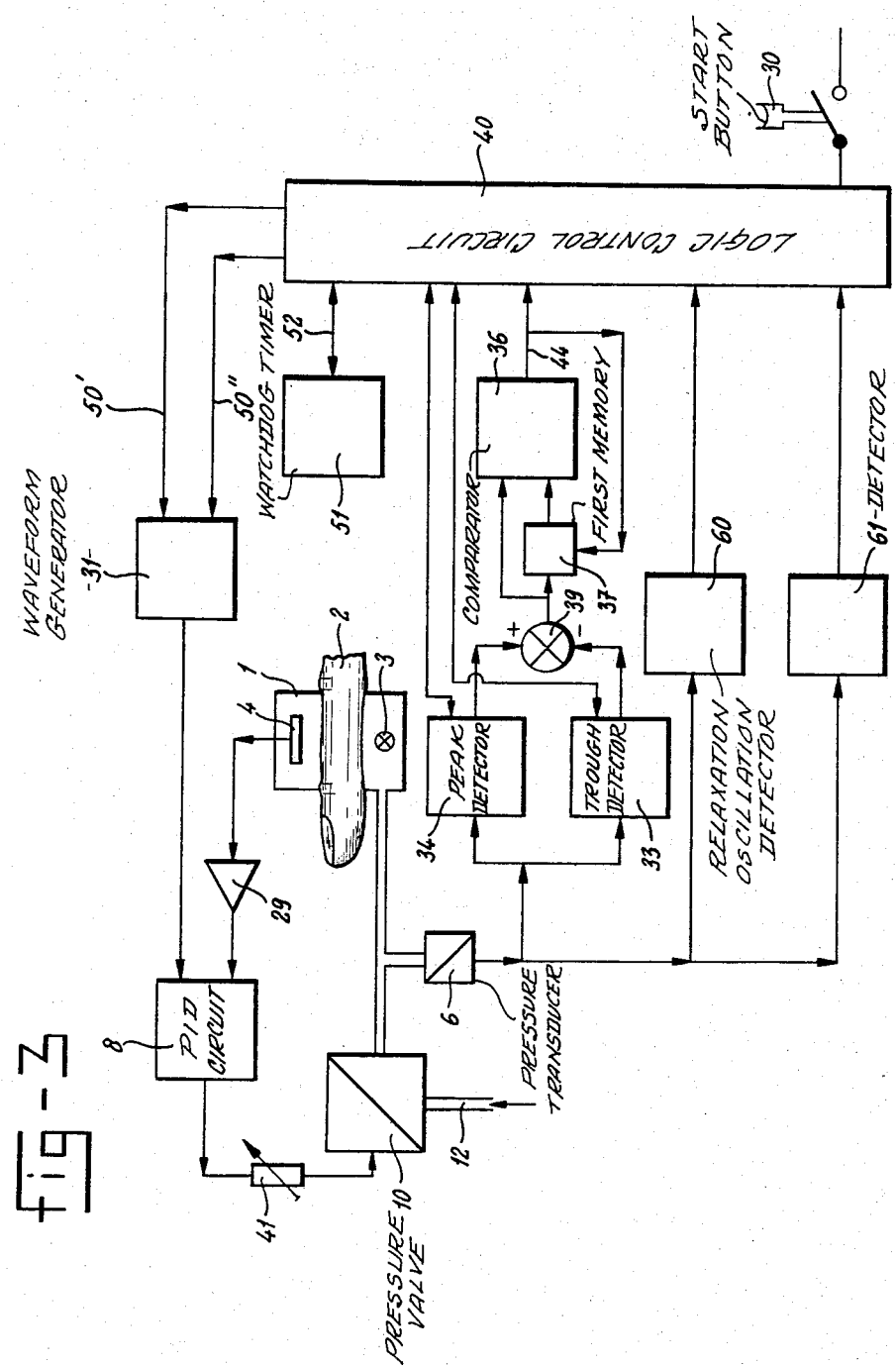

METHOD AND DEVICE FOR CONTROLLING THE CUFF PRESSURE IN MEASURING THE BLOOD PRESSURE IN A FINGER BY MEANS OF PHOTO-ELECTRIC PLETHYSMOGRAPH

BACKGROUND OF THE INVENTION

The invention relates to a method for controlling the cuff pressure in the indirect, non-invasive, continuous measurement of the blood pressure in a finger by using a photo-electric plethysmograph in a fluid-filled pressure cuff, an electronic control circuit and an electric pressure valve, the cuff pressure being controlled by the plethysmographic signal in closed-loop operation by means of a servo-reference level, so that the arterial volume is maintained at a value to be pre-adjusted. The invention relates, furthermore, to a device to carry out said method for the indirect, non-invasive, continuous measurement of the blood pressure in a finger, which device comprises a photo-electric plethysmograph in a fluid-filled pressure cuff and associated light source and light detector, an electric pressure valve and an electronic control circuit provided with a differential amplifier, on the one input and the other input of which respectively the plethysmographic signal and a servo-reference level is supplied. Such a method and device are known from the "Zeitschrift für die gesammte innere Medizine und Ihre Grenzgebiete" VEB Georg Thieme, Leipzig, Volume 31 (1976), pages 1030–1033.

In the method and device known from above periodical for the indirect, non-invasive, continuous measurement of the blood pressure in a finger the pressure of the fluid, e.g. air, in an inflatable cuff around the finger is controlled by means of the signal of the photoelectric plethysmograph and an electric control valve, controlled by a servo loop, in such a way that at any moment the difference between a servo-reference level or nominal value and the plethysmographic signal or real value—safe for a servo-rest error—is zero.

Such a photo-electric plethysmograph is based on the fact that in the chosen wave length range of the light it is, in a first approach, only sensitive to the light absorbing and light diffusing blood in the finger arteries, provided that the cuff pressure is sufficiently high for the other blood vessels to be empty or nearly empty, so that the total arterial blood volume will have to be constant. The artery-wall consists of elastic material so that, when the intra-arterial blood pressure changes, e.g. with the heart beat, the volume of the blood in the arteries will change also, unless the pressure at the outside of the artery, the extra-mural pressure, changes equally at each moment. When a pressure cuff of the right construction and size is put correctly around the finger, the cuff pressure will equal the extra-mural pressure so that, as a result of the described servo-control circuit in the electronic circuit, the intra-arterial pressure can be read at any moment from the cuff pressure, with a determined constant rest difference or constant transmural pressure. This constant rest difference has to be such that the cuff pressure is always lower than or at most equal to the intra-arterial pressure. When this is not the case, the finger arteries under the cuff will coincide or collapse under the influence of the extra-mural pressure being too high. In this case, it is true, the signal of the plethysmograph is also constant, and there is also a one-to-one relation between the cuff pressure on the one side and the intra-arterial pressure on the other side, but resulting from the collapse of the artery the connection with the blood pressure to the supply side is interrupted and the actual arterial blood pressure cannot be read.

From the cited periodical an initial adjustment criterium is known from which it is possible to set the servo-reference level or nominal value in the control loop in such a way that the transmural pressure is zero or practically zero without the finger arteries collapsing. The wall of the artery is then in the unloaded state, and the diameter of the artery is the unstretched diameter just before this artery collapses.

SUMMARY OF THE INVENTION

The object of the invention is now to give a method and a device for an automatic initial adjustment without any manipulation of a human observer, in such a way that a correct level of cuff pressure is guaranteed all the time.

This object is attained by an arrangement wherein for the sake of the initial adjustment, the cuff pressure or the servo-reference level as pre-adjustment quantity is automatically changed continuously in the control range by means of a control wave form to be supplied into the electronic control circuit, that thereby the peak-trough amplitude of the pulsatile plethysmographic signal or cuff pressure signal is detected time and again, and compared with the preceding peak-trough amplitude, the biggest value thereof in the control area and the associated value of the cuff pressure or servo-reference level being stored, which value of cuff pressure or servo-reference level at the end of the initial adjustment is used as set value for the measurement of the blood pressure.

The device according to the invention is characterized in that the electronic circuit further comprises a wave form generator to supply a predetermined control wave form to the circuit; two control loops of which one comprises the differential amplifier having a feedback circuit for the servo-reference level and of which the other comprises a proportionate integrate-differentiate (PID) circuit, the input of which is connected in parallel to the input of the differential amplifier and the output of which is connected to the electric pressure valve; and a logic control circuit.

DETAILED DESCRIPTION OF THE DRAWINGS

The invention will be explained in detail with reference to the drawings, in which:

FIG. 1 shows a block diagram of the device applied in the known method; and

FIGS. 2 and 3 show block diagrams of possible embodiments of the device according to the invention applicable in the method according to the invention.

DETAILED DESCRIPTION

The known device shown in FIG. 1 has a photo-electric plethysmograph in a pressure cuff 1, which can be put around finger 2, and a light source 3 and light detector 4 both mounted at the inner side of the pressure cuff. The plethysmographic or volume-changing signal outputted by the light detector 4 is supplied via line 5b to a differential amplifier 7, to which also an adjustment or servo-reference level is supplied from the adjustment means 13. The output signal of the differential amplifier 7, in closed-loop operation, is supplied to a PID-circuit 8. In open-loop operation, i.e. open control loop, a pressure adjustment signal is supplied to the PID circuit 8 from the manual adjustment means 11. The output signal of the PID circuit controls the electric pressure valve or the electro-pneumatic transducer 10 in such a way that pressurized fluid 12 e.g. gas or air, from a pressurized source is adjusted to the desired pressure which is conveyed via line 5a to the pressure cuff 1. By means of a pressure transducer (manometer) 6, connected to the output of the electric pressure control valve 10, the pressure can be read or recorded.

FIG. 2 shows an embodiment of the device according to the invention, with which the method according to the invention can be carried out. The same reference numbers refer to those parts that correspond to the parts in FIG. 1 with the same functions.

When pressing the start button 30, the device is placed in state a, i.e. in position a of switch S1, by means of switching control signal 47 from the logic control circuit 40. Hereby a control wave form from the wave form generator 31 is supplied via switch S1 to the electric pressure valve 10, to which also pressurized fluid 12 e.g. air, from a pressurized source 12. Based upon the control wave form, the cuff pressure of the cuff 1 is set to a starting pressure of e.g. 30 mm Hg. At each following trigger pulse 50 from logic control circuit 40 the next step is adjusted in the wave form generator 31, which step for instance has a step value of 10 mm Hg. The pulsatile plethysmographic signal is supplied via line 5b and the amplifier 29 to the one input of a differential amplifier 32. An integrator 35 in the feed-back circuit from the output to the other input of differential amplifier 32 provides for the output signal of the differential amplifier to be continuously around zero-value. The pulsatile plethysmographic signal subsequently is supplied to a parallel circuit of a peak detector 34 and a trough detector 33.

After detection of a trough according to the diastolic level and subsequent detection of a peak according to the systolic level, and when, after termination of same, a ready signal 43, 42 respectively is supplied to the control circuit 40, the differential amplitude is supplied to a first memory 37 via a differential circuit 39. The differential amplitude is not stored in this differential circuit yet. Each running differential amplitude is compared with the preceding one by means of a comparator circuit 36. When the running differential amplitude is larger than the preceding one, the cuff pressure control value then present (from waveform generator 31 via switch S1) is caused to be stored in a second memory 38 by means of a control signal 44 from comparator 36. At the same time, as a result of the control signal 44 the differential amplitude is stored in first memory 37, and both detectors 34 and 33 are reset by the logic control circuit 40 via the reset signals 48 and 49.

Hereafter, the control wave form of the wave form generator 31 is increased with the step value under the influence of the control pulse 50, after which the next trough-peak detection is carried out.

In this way, the total control pressure range between starting and final pressure, e.g. from 30 to 200 mm Hg, is run through, while in the memory 38 that cuff pressure value is maintained, at which the difference between trough and peak level in the plethysmographic signal is at its maximum. It is remarked that the pulsations of the plethysmographic signal arise as a result of the pulsating heart action, i.e. of the pulsating changes of the volume, which must be opposed by the extramural or cuff pressure in closed-loop operation.

After a last measurement has been effected in the open-loop position a of switch S1, the device is subsequently put in state b, i.e. in position b of switch S1, by a switching control signal 47 from the logic control circuit 40. The cuff pressure now has a value at which the pulsations in the plethysmographic signal are at maximum value. For a given period of time, e.g. 5 seconds, which period of time is at least three times the time constant of the circuit differential amplifier-integrator, said differential amplifier-integrator circuit now has the opportunity to adjust its output signal at the time average level in the plethysmographic signal.

Hereafter the device is put into state c, i.e. in position c of the switch S1, under the influence of the control circuit 40, whereby this action closes the PID control loop by means of the switch S1 in position c. The PID control loop in its responses is much faster, for example a factor 100 times, than the integrator loop, so that said PID control loop now maintains the output signal of the differential amplifier 32 at zero, whereby the integrator 35 does not change its output or servo-reference level any more. The cuff pressure will follow the intra-arterial pressure dynamically, which can be read by means of pressure transducer (manometer) 6.

The final pressure in the control-pressure range is defined by the requirement that it has to be higher than the highest average arterial pressure that can occur in any person. Likewise, the initial pressure in the control pressure range is defined by the lowest pressure occurring. Consequently, at a cuff pressure, approximately equal to the average pressure, maximal pulsations will occur in the plethysmographic signal or plethysmogram. In this case, the arterial volume shows a maximal variation between the volume in the collapsed state during diastole, when the intra-arterial pressure is smaller than the cuff pressure, and the volume in normal open state during systole, when the intra-arterial pressure is larger than the cuff pressure.

At low average pressure, in general a proportionate reduced pulse pressure, i.e. the difference between systolic and diastolic pressure level, will occur, so that at a fixed pressure step value only few measurements can be effected for the trough peak values of the plethysmographic signal. As at a cuff pressure above the systolic pressure no plethysmographic signal occurs any more, and as the optimal initial adjustment pressure can only be defined roughly and inaccurately, it is preferred to exponentially increase the pressure steps and with these the pressure levels by small steps at the beginning and by larger steps at the end of the control range. This can be realized simply by a fixed potentiometer having switchable exponential taps.

In the automatic initial adjustment described above, the pressure in open-loop operation is changed stepwise. It is also possible to start from a monotonically continuously increasing wave-form supplied by the wave form generator, so that said pressure also shows a monotonically continuous increase, either linearly in time or exponentially, or otherwise. In this state there is no need of a control pulse 50 for the wave form generator, as at each trough and peak detection, associated with each pulsation of the heart action, the current cuff pressure value from the wave form is stored.

This solution simplifies the logic control circuit 40, but has the disadvantage that the acceleration of the method possible with a person having a higher heart beat frequency and stepwise course is not taken into consideration. Also the value of the cuff pressure, at which the maximal differential amplitude in the plethysmographic signal is observed, is less unambiguous. On the other side, in a steplike course of the wave form a certain quantisation occurs in the pressure which also causes some uncertainty.

Due to the fact that there is no plethysmographic signal present any more, above the systolic level the trough and peak detectors will not be able any more to establish a value at those pressure levels, so that the initial adjustment cannot be finished. In order to prevent this, a so-called watchdog timer 51 is installed which, after a defined fixed time, e.g. 1.5 seconds or longer than the lowest pulse repetition period of the heart, terminates state a, and subsequently realizes the transition to state b and then to state c. At a relatively low average arterial pressure this can even reduce the initial adjustment.

Normally the watch dog timer 51 is reset to zero at each detected pulsation of the plethysmographic signal via the line 52. It is important that state a is broken off only after at least at a pressure level of e.g. 100 mm Hg another measurement has been effected in the plethysmographic signal.

Large differences in elasticity of artery wall and in normal diameter of finger arteries can occur between different persons. This influences the effective amplification in the servo-control loop. Also between the pressure cuffs mutually the sensitivities of the photo-electric plethysmographs can differ with the same effect. At too high an amplification the servo-control loop becomes unstable. In order to prevent this the loop amplification, via the line 46 can be adjusted by means of the divider circuit 41 inversely proportionate to the trough-peak amplitude in the plethysmographic signal when the control loop is open, such as is determined in state a and is stored in memory 37.

In state a of the switch S1, i.e. in open-loop operation, a certain slight and in general hardly objectionable distortion in the pulsating plethysmographic signal will occur due to the presence of the integrator 35 for the continuous adjustment of the servo-reference level and consequently of the average plethysmographic signal to zero. A refinement of the electronic control circuit in the servo loop consists in this that in state a the integrator 35 is accelerated very strongly, e.g. by a factor 100, during a certain time, e.g. 50 ms. After this period the integrator 35 is slowed down very strongly, e.g. again by a factor 100, with respect to the normal value. Due to this the level during the first period of e.g. 50 ms is, as it were, clamped for the rest of the period. For this purpose the integrator 35 is provided with a switchable time constant which can be realized simply by switching three integration capacitors one-sidedly between earth and input of the integrator respectively.

As observed, the above method and device make use of the heart action, in this that the natural pulsations in the arterial pressure cause the pulsations in the plethysmographic signal or plethysmogram. In defined circumstances, however, it may happen during measurement of the blood pressure in a finger that these pulsations do not occur, e.g. when the patient is connected to a heart-lung machine. In this case the method could not be used. This situation of failing of the pulsations can be established automatically on the one side by means of the continuous absence of the plethysmographic signal, but on the other side it can be established by a human observer by setting a switch.

A plethysmographic signal can, however, be obtained by replacing the natural intra-arterial pressure pulsations by artificially effected pulsations. This can be realized simply by superposition of artificial pulsations, in the states a and b of the initial adjustment, on the determined pressure levels of the wave form generator supplied to the cuff. This can be done by means of an additional pulse generator 53 connected to the positions a and b of the switch S1. The desired transmural pulsations are then generated externally under control of a control signal 45 coming from the logic circuit. In order to supply a plethysmographic signal in the correct phase to the trough and peak detectors and other component parts, the pulsation to be superposed has to be supplied in counter-phase to the inputs a and b of the switch S1 as an increasing pressure in diastole and a decreasing pressure in systole. This required wave form of the generator 53 can for instance be obtained by means of a simulator as described in the article "Variable heartrate electronic simulator for some haemodynamic signals" in Med.Biol. Engineering (1973), pages 214–216. It is, however, also sufficient to supply a stylized wave in the form of a saw tooth having a rise time in diastole of e.g. 600 ms and a fall time in systole of e.g. 60 ms. A suitable amplitude is e.g. 60 mm Hg peak to peak.

The method steps described above can be carried out—apart from the described embodiment of the electronic control circuit—also with a microprocessor.

In the automatic initial adjustment method and device described above, the control loop is first opened, whereby the initial adjustment pressure range is passed through stepwise. The trough-peak amplitude of the plethysmographic signal is determined and its maximal value is stored in a memory 37. This adjustment is the so-called "open" adjustment method.

Another "closed" or dual initial adjustment method is possible in principle, and is shown in FIG. 3.

One starts from a closed state, i.e. that the switch S1, not shown in FIG. 3, is in position c. The output circuit of the PID circuit 8 is connected directly to the electric pressure valve 10 via the switch. In this dual initial adjustment method the servo-reference level is changed, e.g. stepwise, by the wave form generator 31, which is now connected instead of the integrator 35. This stepwise change can be realized under influence of the control circuit 40 by means of the control signals 50', 50" with rising or falling steps. The detection circuit is now connected to the output of the pressure transducer (manometer) 6 instead of to the output of the differential amplifier 32. The output signals of the trough detector 33 and the peak detector 34 are supplied again as a trough-peak differential amplitude via the differential circuit 39 to the first memory 37 and to the comparator circuit 36. This means that at each detection of the systolic and diastolic level of the pulse wave pressure, the servo-reference level is increased stepwise via the wave form generator. Hereby the maximal value of the trough-peak differential amplitude is stored in the first memory 37, and that level of the wave form generator 31 is maintained in a second memory (which second memory, in this embodiment, is part of the logic circuit 40) at which the maximal pulse pressure amplitude occurs.

As at low servo-reference levels, pressure pulsations will not yet occur, the watch dog timer 51 is of importance in the beginning of the initial adjustment in order to limit the measuring time. The watch dog timer is reset back via the liner 52 by the logic control circuit or said timer is warned from this time generator to proceed to the following switching step.

In this dual initial adjustment method another set of detectors 60 and 61 is used. The detector 60 serves to detect a relaxation-oscillation phenomenon in the pressure and the detector 61 serves to detect an uninterrupted pressure of 200 mm Hg or more for a period of e.g. one second. If one of these detectors or both react, the initial adjustment method is to be stopped at a level of one or two steps below the current servo-reference level.

The relaxation-oscillation detector 60 must respond when the observed first derivative of the cuff pressure to time (dP/dt) is bigger than a value which can occur at best in normal pressure wave forms. A good value is e.g. 3000 mm Hg/s or 400 kPa/s.

The step curve can have linear steps in magnitude of e.g. 2% of the full scale value.

In this dual initial adjustment method there is really no good criterion for the automatic adjustment of the loop amplification other than having the loop go into oscillation, after which one has to readjust quickly.

Summarizing, the criterion for adjusting the stop of the stepwise adjustment curve will have to be:
pulse pressure smaller than in the preceding step, or
dP/dt bigger than 3000 mm Hg/s, or
p>200 mm Hg for one second.

In all these cases the step generator must be stopped and must be adjusted even one or two steps lower than the stop level.

We claim:

1. An improved method for controlling cuff pressure in an indirect, non-invasive, continuous measurement of blood pressure in a finger by using a photo-electric plethysmograph providing a pulsatile plethysmographic signal and used with a fluid-filled pressure cuff, an electronic control circuit having an open and closed-control loop operation, an electric pressure valve connected to said cuff and a cuff pressure transducer providing a cuff pressure signal, the cuff pressure being controlled by the plethysmographic signal in closed-loop operation by means of a servo-reference level, so that the arterial volume is maintained at a preadjusted value, wherein the improvement includes the steps of:
    continuously changing, within a control range, for initial open loop adjustment, the cuff pressure or the servo-reference level by means of a control wave form provided to the electronic control circuit;
    periodically detecting each peak-trough differential amplitude of the pulsatile plethysmographic signal or cuff pressure signal;
    comparing each said peak-trough differential amplitude with the preceding peak-trough differential amplitude; and
    storing the associated value of peak-trough differential amplitude in the control range and the associated value of the cuff pressure or servo-reference level, and using said associated value of cuff pressure or servo-reference level at the end of the initial adjustment as the for set value measurement of the blood pressure after initial open-loop adjustment.

2. A method according to claim 1 further comprising, before the step of continuously changing, the step of setting the cuff pressure to a value between previous diastolic and systolic pressure, such that the pulsatile plethysmographic signal is at maximum, and wherein the step of continuously changing comprises the step of changing the cuff pressure stepwise whereby each following pressure step increase is initiated by termination of the current peak-trough detection of the pulsatile plethysmographic signal.

3. A method according to claim 2 wherein the step of stepwise changing comprises the step of changing the cuff pressure in exponentially increasing pressure steps.

4. A method according to claim 1 further including the step of adjusting loop amplification in closed-loop operation in inverse proportion to the peak-trough differential amplitude in the pulsatile plethysmographic signal in open-loop operation.

5. A method according to claim 1 further including the step, in absence of natural intra-arterial pressure pulsations, of superposing artificial pressure pulsations on the control wave form provided to the electronic control circuit.

6. In a device for controlling cuff pressure in an indirect, non-invasive, continuous measurement of blood pressure in a finger, which device comprises a photo-electric plethysmograph providing a pulsatile plethysmographic signal and used with a fluid-filled pressure cuff and associated light source and light detector, an electric pressure valve connected to the cuff, a cuff pressure transducer providing a cuff pressure signal and an electronic control circuit having an open and closed control-loop operation and including a differential amplifier having a first and second inputs respectively receiving the plethysmographic signal and a servo-reference level, the improvement comprising:
    a wave form generator which supplies a control wave form, continuously changing in a control range, to the electronic control circuit;
    two control loops of which one comprises the differential amplifier having a feed-back circuit for the servo-reference level and the other of which comprises a proportionate integrate-differentiate (PID) circuit, the input of which is connected in parallel to an input of the differential amplifier and the output of which is connected to the electric pressure valve; and
    a logic control circuit connected to said wave form generator and to said two control loops.

7. A device according to claim 6 in which one of the two control loops is further connected to an adjustment loop comprising a detection circuit which detects the pulsatile plethysmograhic or cuff pressure signal and a memory circuit which temporarily stores successive peak-trough differential amplitudes of said pulsatile signal and the associated value of cuff pressure or servo-reference level.

8. A device according to claim 7 further comprising a switch with open and closed loop positions, which switch is connected at an output pole thereof to the electric pressure valve, at a first input pole thereof for open-loop operation to the wave form generator, and at a second input pole thereof, for closed-loop operation, to the input of the PID circuit, respectively, the adjustment loop having the detection circuit and memory circuit being coupled after the control loop having the differential amplifier.

9. A device according to claim 8 in which the detection circuit comprises a parallel circuit of a peak detector and a trough detector, in which the memory circuit comprises a first memory for the peak-trough differential amplitudes and a second memory for the cuff pressure values, the device further including a comparator circuit which compares each detected peak-trough differential amplitude with the preceding peak-trough differential amplitude and in case of exceeding same to store the current differential amplitude in the first memory and the associated cuff pressure value from the control wave form in the second memory.

10. A device according to claim 9 in which the feedback circuit of the differential amplifier comprises an integrator, and wherein the switch has a further input pole, connected in open-loop operation to the second memory, in order to supply, under control of the logic control circuit, after cuff pressure has passed through the control range in one open-loop operation, the cuff pressure value corresponding to the maximum peak-trough differential amplitude to the electric pressure valve during a time sufficient to have the differential amplifier-integrator adjust its output signal to a time average level, after which the switch changes to its closed-loop position.

11. A device according to claim 9 in which the output of the first memory is also connected to control a further included divider circuit, coupled between the output of the PID-circuit and the switch, in order to adjust the loop amplification in the PID control loop in inverse proportion to the peak-trough differential amplitude of the plethysmographic signal in open-loop operation.

12. A device according to claim 9 in which the wave form generator is a step generator and in which the peak detector and the trough detector, at the end of each peak and trough detection respectively, supply a ready-signal to the logic control circuit, which subsequently triggers the step generator for the next step.

13. A device according to claim 12 in which the step generator is embodied such that the step curve shows an exponentially increasing step.

14. A device according to claim 6 in which the wave form generator is embodied such that it supplies a monotonically continuously increasing control wave form.

15. A device according to claim 7 in further including pulsation generator used in order to superpose, in the absence of natural intra-arterial pressure pulsations, artificial pressure pulsations on the control wave form of the wave form generator to be supplied to the input of said switch.

* * * * *